United States Patent [19]

Greenberg

[11] Patent Number: 5,599,185
[45] Date of Patent: Feb. 4, 1997

[54] DENTAL IMPLANT HEALING ABUTMENT

[75] Inventor: Alex M. Greenberg, New York, N.Y.

[73] Assignee: Greenberg Surgical Technologies, LLC, New York, N.Y.

[21] Appl. No.: 314,600

[22] Filed: Sep. 28, 1994

[51] Int. Cl.⁶ .................................................. A01C 8/00
[52] U.S. Cl. ........................................ 433/173; 433/174
[58] Field of Search ................................. 433/172, 173, 433/174, 175, 176

[56] References Cited

U.S. PATENT DOCUMENTS

| | | |
|---|---|---|
| 3,919,773 | 11/1975 | Freeman . |
| 3,971,134 | 7/1976 | Bokros . |
| 3,987,499 | 10/1976 | Scharbach et al. ............... 3/1.91 |
| 4,186,486 | 2/1980 | Gordon ............................. 433/201 |
| 4,217,100 | 8/1980 | Edelman .......................... 433/176 |
| 4,244,689 | 1/1981 | Ashman ........................... 433/175 |
| 4,276,026 | 6/1981 | Edelman .......................... 433/176 |
| 4,279,598 | 7/1981 | Scheicher ......................... 433/173 |
| 4,330,891 | 5/1982 | Brånemark et al. .............. 3/1 |
| 4,370,136 | 1/1983 | Widman et al. ................. 433/217 |
| 4,439,152 | 3/1984 | Small ................................ 433/173 |
| 4,657,510 | 4/1987 | Gittleman ........................ 433/173 |
| 4,713,003 | 12/1987 | Symington et al. ............. 433/173 |
| 4,713,004 | 12/1987 | Linkow et al. .................. 433/174 |
| 4,722,688 | 2/1988 | Lonca .............................. 433/173 |
| 4,738,623 | 4/1988 | Driskell ............................ 433/173 |
| 4,772,204 | 9/1988 | Söderberg ....................... 433/174 |
| 4,793,808 | 12/1988 | Kirsch ............................. 433/173 |
| 4,812,120 | 3/1989 | Flanagan et al. ................ 433/173 |
| 4,832,601 | 5/1989 | Linden ............................ 433/173 |
| 4,850,870 | 7/1989 | Lazzara et al. ................. 433/174 |
| 4,854,872 | 8/1989 | Detsch ............................. 433/173 |
| 4,856,994 | 8/1989 | Lazzara et al. ................. 433/173 |
| 4,907,969 | 3/1990 | Ward ................................ 433/173 |
| 4,955,811 | 9/1990 | Lazzara et al. ................. 433/173 |
| 4,988,292 | 1/1991 | Rosen .............................. 433/8 |
| 4,993,950 | 2/1991 | Mensor ............................ 433/173 |
| 5,000,685 | 3/1991 | Brajnovic ......................... 433/173 |
| 5,015,186 | 5/1991 | Detsch ............................. 433/173 |
| 5,030,095 | 7/1991 | Niznick ........................... 433/173 |
| 5,040,982 | 8/1991 | Stefan–Dogar ................. 433/169 |
| 5,069,622 | 12/1991 | Rangert et al. ................. 433/173 |
| 5,071,350 | 12/1991 | Niznick ........................... 433/173 |
| 5,087,200 | 2/1992 | Brajnovic et al. .............. 433/173 |
| 5,106,300 | 4/1992 | Voitik ............................... 433/173 |
| 5,108,288 | 4/1992 | Perry ................................ 433/173 |
| 5,116,225 | 5/1992 | Riera ................................ 433/173 |
| 5,125,839 | 6/1992 | Ingber et al. .................... 433/169 |
| 5,135,395 | 8/1992 | Marlin .............................. 433/174 |
| 5,169,309 | 12/1992 | Staubli et al. ................... 433/174 |
| 5,178,539 | 1/1993 | Peltier et al. . |
| 5,213,500 | 5/1993 | Salazar et al. .................. 433/169 |
| 5,238,405 | 8/1993 | Marlin .............................. 433/173 |
| 5,281,140 | 1/1994 | Niznick ........................... 433/172 |
| 5,297,963 | 3/1994 | Dafatry ............................ 433/172 |
| 5,302,125 | 4/1994 | Kownacki ........................ 433/172 |

FOREIGN PATENT DOCUMENTS

| | | | |
|---|---|---|---|
| 0288702 | 11/1988 | European Pat. Off. | ............ 433/173 |
| 4112200 | 6/1993 | Germany | ............ 433/174 |

*Primary Examiner*—Nicholas D. Lucchesi
*Attorney, Agent, or Firm*—Meltzer, Lippe, Goldstein, et al.

[57] ABSTRACT

An improved healing abutment includes a deformable cap which rotationally contacts a surface connected to an implant fixture. The deformable cap maybe selectively positioned at a desired angle with respect to the implant fixture. An overcap is positioned over the deformable cap. The overcap has an inner surface which contacts and compresses the deformable cap into secure contact with the surface connected to the implant fixture at the desired angle. This secures the overcap in position at the desired angle, which allows the soft tissue to heal except where the dental prosthesis will be located.

13 Claims, 8 Drawing Sheets

DENTAL IMPLANT HEALING ABUTMENT

FIELD OF THE INVENTION

The present invention relates to a dental implant healing abutment and, more particularly, to a dental implant healing abutment having improved rotational freedom and which permits soft tissue to heal closer to the desired location of a dental prosthesis.

BACKGROUND OF THE INVENTION

Dental prosthetic devices are becoming increasingly popular and are rivaling the use of removable dentures, partial dentures, or conventional bridges in replacing lost teeth.

A conventional dental implant device typically comprises two components, an implant fixture and an abutment. An implant fixture is imbedded into a patient's maxilla or mandible bone. An abutment is connected to the fixture and typically forms a support for a prosthesis, i.e., a crown, denture, partial bridge, or bridge. The implant fixture may be surgically implanted into the bone at various angles depending on several factors, such as the number of implants being placed into a corresponding section of edentulous (toothless) bone; the portion of the edentulous bone best suited to successfully support the implant; and the angle chosen by the dental professional in placing the implant. The abutment, however, must be aligned so that the dental prosthesis it will receive is generally parallel with other surrounding teeth, regardless of the angle at which the implant fixture is placed in the bone.

FIG. 1 shows a conventional dental implant system using the Branemark system where the implant fixture does not extend above the soft tissue. This system is described in *Tissue Integrated Prosthesis*, P. I. Branemark, G. A. Zarb, and T. Alberktsson, Chicago Quintessence Publishing Co. (1985). This is known as a submergible implant system. The mandible or maxilla 50, covered with soft tissue 52, has a number of implant fixtures 60 screwed into the bone 50 at various angles. Each implant has an abutment 65. The abutments are at generally parallel angles and, in this figure, support a support bar 67 retained on the abutments by screws 69.

It is preferable for the abutment to be selectably angled with respect to the implant fixture. For example, implant fixture 60a of FIG. 1 is implanted at an angle different than the angle necessary for proper alignment of the dental prosthesis. Thus, the abutment 65a must be able to be angled with respect to the implant fixture 60a so that a prosthetic tooth, or other prosthetic device, may be mounted at the proper angle with respect to the surrounding teeth or other prosthetic devices.

FIG. 2 is a cross-sectional view of a conventional dental implant in place in a patient's bone. A dental implant fixture 60 is screwed into place in a patient's mandible or maxilla 50. (In the case of an extraoral epithesis, the implant fixture is located in the appropriate bone.) This implant fixture 60 has an internal threaded opening which receives an abutment 65. The abutment has a head 67 shaped to receive a prosthetic tooth 70 (or other prosthetic device). Growing around the prosthetic tooth and implant above the mandible 50 is soft tissue 52. The soft tissue includes several layers including the epithelium layer 53 at the outer surface of the soft tissue; connective tissue 54; and the periosteum 56 located adjacent to the bone 50.

The dental implant procedure is done in several steps. This procedure is described in detail in *Tissue Integrated Prosthesis*, P. I. Branemark et al. First, a surgeon makes an incision in a patient's soft tissues 52, exposing the bone 50. A series of drilling procedures establishes a receptor site hole of a particular diameter in the bone. This is known as an osteotomy site. This osteotonomy site may be tapped to have threads, or the threads may be cut by a "self tapping" implant fixture. In either event, an implant fixture 60 is secured into the bone. A cover screw is screwed into the implant fixture internal thread to prevent soft tissue growth into the fixture internal thread. Several months pass to allow the bone to solidify around the implant fixture.

After six months, the soft tissue is again opened and the cover screw is removed. A healing abutment is screwed into the threaded opening in the implant fixture to perform two functions. First, the healing abutment closes the threaded opening. Second, the healing abutment allows the soft tissue to heal around the area of the incision, and can leave an opening or contour for the abutment and prosthetic tooth to be placed, or the tissue closes completely over the healing cap. The soft tissue heals to a desired contour. After several weeks or months, the healing abutment is removed. A post, standard abutment, or angulated abutment is positioned in the threaded opening. A dental prosthesis is positioned onto the post or abutment.

FIG. 3 shows a conventional healing abutment in place in a patient. A dental implant fixture 60 is implanted in a mandible 50. A dental implant healing abutment 72 is screwed into a threaded opening 74 in the fixture 60. The soft tissue 52 will heal around the superior portion of the fixture and the healing abutment. Because the implant fixture 60 may not have the same longitudinal axis as the standard abutment (and thus the prosthetic tooth), the healing abutment is designed to allow for a variety of rotational angles. As shown in FIG. 3, the healing abutment 72 has a conical shape extending upward from the superior portion of the implant fixture 60. This conical shape prevents the soft tissue 52 from healing around the healing abutment so that an unobstructed opening exists so that the abutment and dental prosthesis may be placed at a variety of angles with respect to the fixture 60. FIG. 3 shows (slightly exaggerated) extreme angles $\alpha_1$ and $\alpha_2$.

FIG. 4 illustrates one drawback of this conventional healing abutment. After the bone has solidified around the implant fixture 60 and the soft tissue has healed around the healing abutment 72, the healing abutment is removed and replaced with a post or abutment 65. The post or abutment is adjusted to the proper angle and a prosthetic tooth 70 is inserted onto the post or abutment 65. The healing abutment leaves a gap 74 around the base of the prosthetic tooth 70, which will never fill in. This gap 74 has several disadvantages. First, food particles and the like may become lodged in the gap and lead to infection and possibly gum disease. Secondly, the gap 74 is visible and is aesthetically unpleasant, particularly for front teeth which are easily observable, for example, when smiling.

Therefore, it is an object of the present invention to provide a healing abutment which allows soft tissue to heal at a proper angle without leaving an undesirable gap or undesirable contours.

SUMMARY OF THE INVENTION

These and other objects are obtained by an improved dental implant healing abutment. The improved healing abutment includes a deformable cap which rotationally contacts a surface connected to an implant fixture. The deformable cap may be selectively positioned at a desired angle with respect to the implant fixture. An overcap is positioned over the deformable cap. The overcap has an external configuration generally the same as a dental prosthesis and an inner surface which contacts and compresses the deformable cap into secure contact with the surface connected to the implant fixture at the desired angle. This secures the overcap in position at the desired angle, which allows the soft tissue to heal except where the dental prosthesis will be located.

BRIEF DESCRIPTION OF THE DRAWINGS

These and other features of the invention will be made apparent by the following drawings, wherein.

DETAILED DESCRIPTION OF REFERRED EMBODIMENTS

Figure 1:
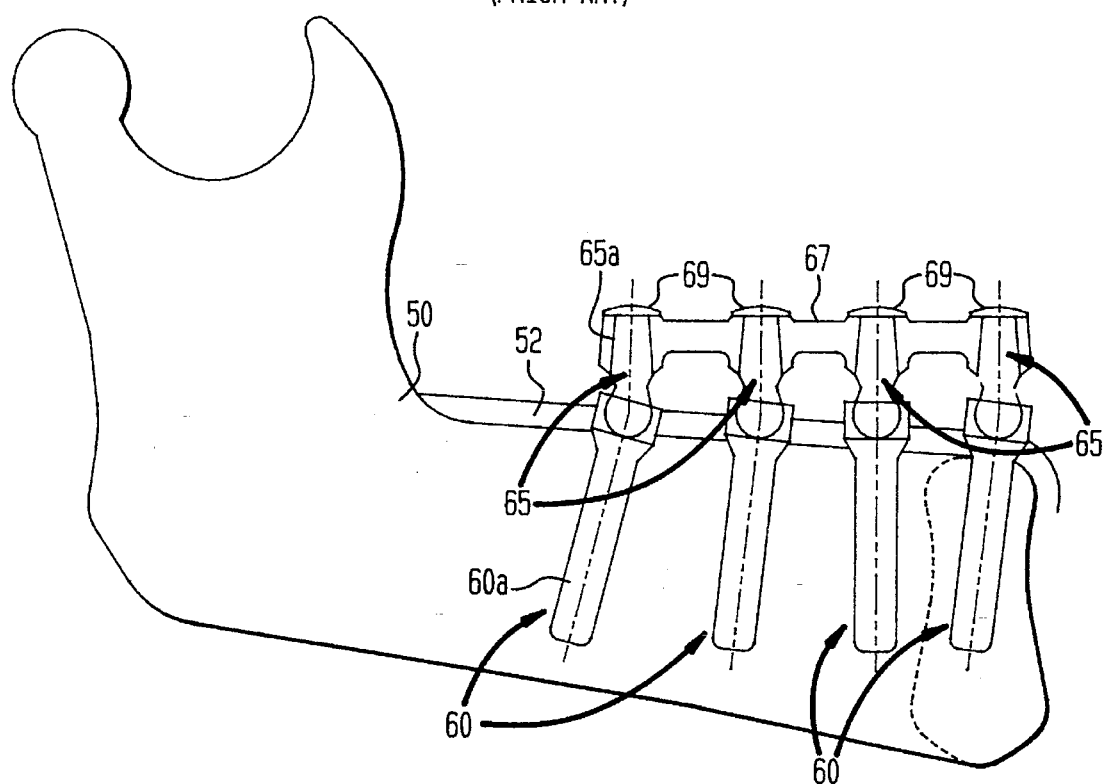
FIG. 1 shows a conventional dental implant system.
Figure 2:
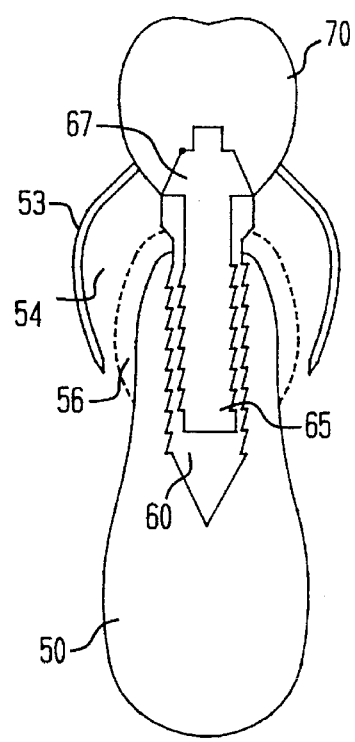
FIG. 2 is a cross-sectional view of a conventional dental implant and prosthetic tooth.
Figure 3:
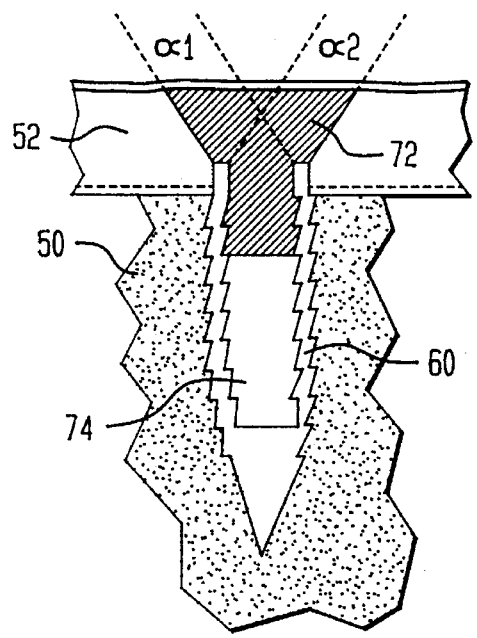
FIG. 3 shows a conventional dental implant fixture and healing abutment in place in a patient.
Figure 4:
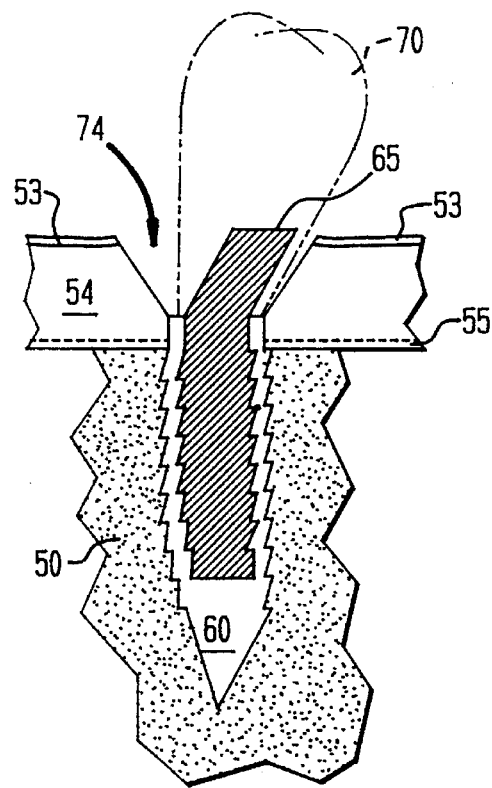
FIG. 4 is a cross-sectional view of a conventional dental implant and prosthetic tooth in a patient after using the healing abutment shown in FIG. 3.
Figure 5:
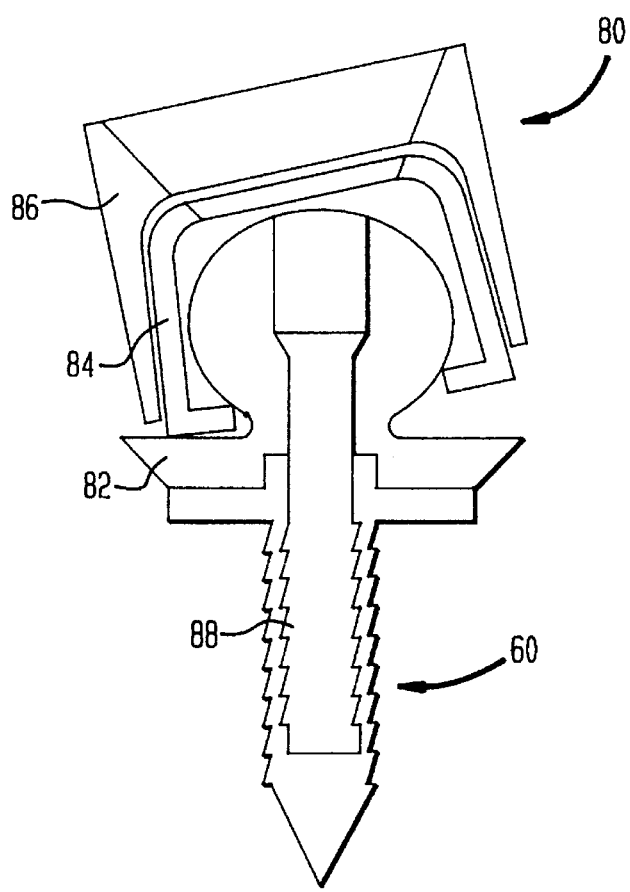
FIG. 5 is a cross-sectional view of a dental implant fixture having a healing abutment according to the present invention.

FIG. 5 shows an illustrative embodiment of a dental implant fixture 60 having a healing abutment 80 according to the present invention. The healing abutment comprises a first cap having a contact surface 82 connected to the fixture 60; a deformable cap 84 which rotationally contacts the contact surface; an overcap 86 having an inner surface which compresses against the deformable cap 84; and a retaining screw 88. A second retaining screw holds deformable cap 84 and overcap 86 in position with respect to the first cap 82, but is omitted from this figure for clarity.

Figure 6:
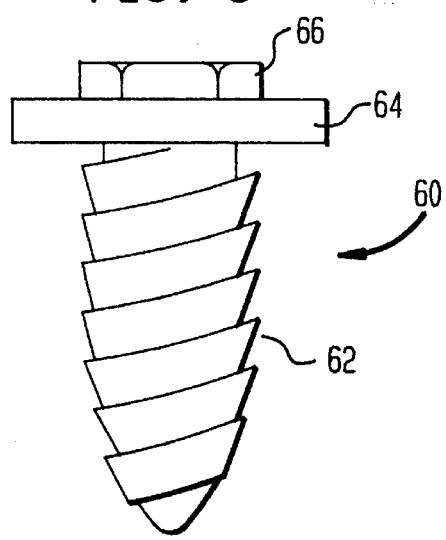
FIG. 6 is a front elevational view of a dental implant fixture which is used with the present invention.
Figure 7:
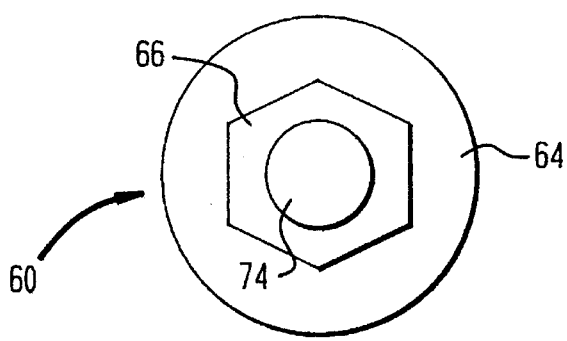
FIG. 7 is a top view of the dental implant fixture of FIG. 6.
Figure 8:
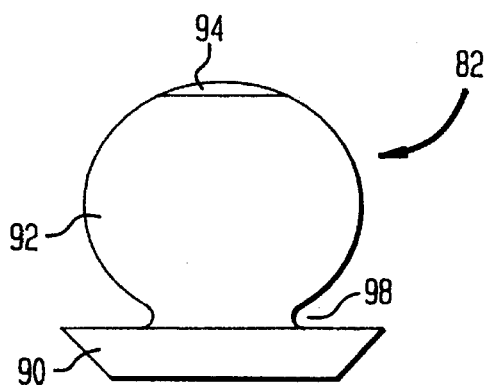
FIG. 8 is a front elevational view of a first cap according to the present invention.
Figure 9:
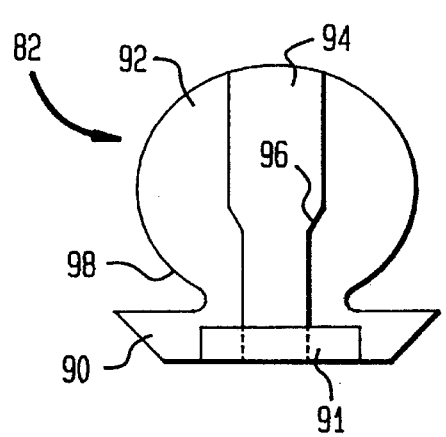
FIG. 9 is a cross-sectional view of the first cap of FIG. 8.
Figure 10:
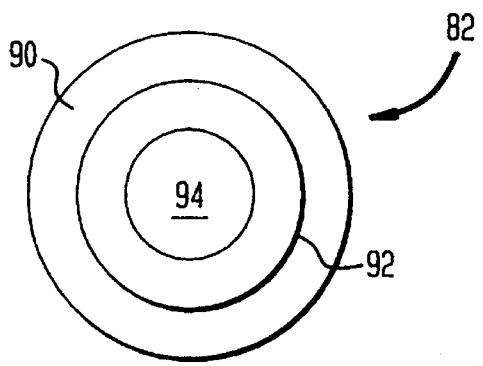
FIG. 10 is a top view of the first cap of FIG. 8.
Figure 11:
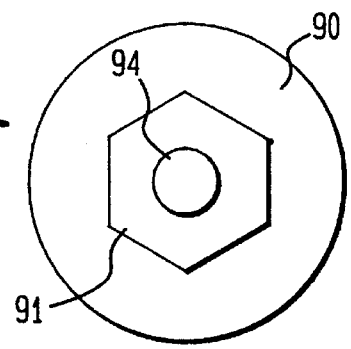
FIG. 11 is a bottom view of the first cap of FIG. 8.
Figure 12:
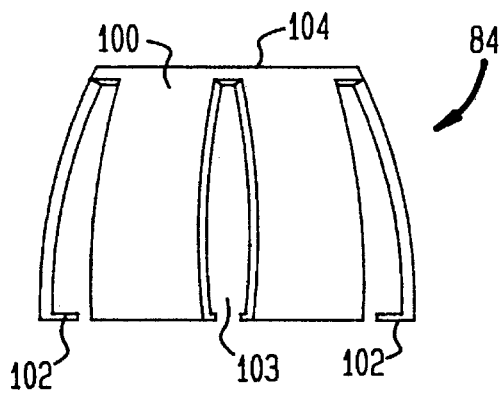
FIG. 12 is a front elevation view of a deformable cap according to the present invention.
Figure 13:
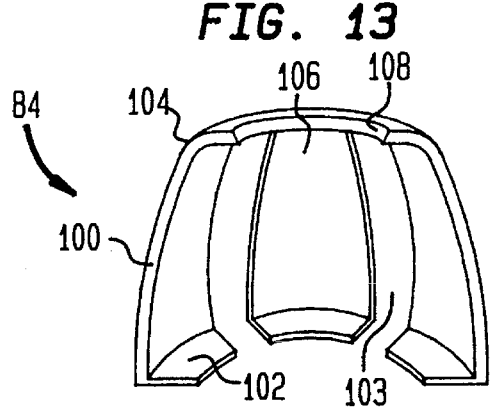
FIG. 13 is a cross-sectional view of the deformable cap of FIG. 12.
Figure 14:
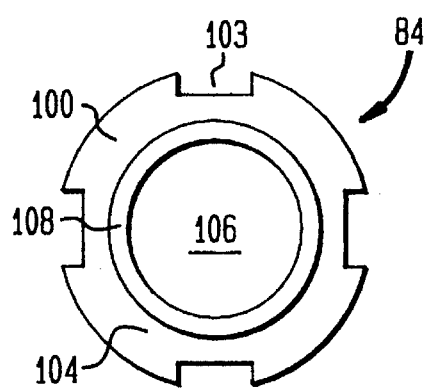
FIG. 14 is a top view of the deformable cap of FIG. 12.
Figure 15:
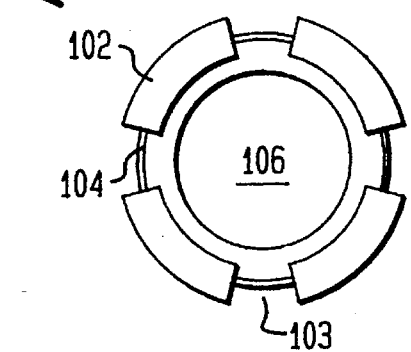
FIG. 15 is a bottom view of the deformable cap of FIG. 12.

FIGS. 6 and 7 illustrate a dental implant fixture 60 which may be used with a healing abutment of the present invention. This dental implant may be a commercially available implant fixture sold by, for example, Implant Innovations Inc., a corporation located in West Palm Beach, Fla. or Nobelpharma, a corporation located in Chicago, Ill. An illustrative implant fixture has a threaded body 62, a circular portion 64, and a hexagonal-shaped head 66, which allows the dental implant fixture to be implanted with a hex driver. The implant fixture has a threaded opening 74 to receive threaded components such as healing abutments, abutments, and posts. The implant fixture may be made of titanium or other materials suitable for dental implants.

FIGS. 8–11 show an illustrative embodiment of the first cap having a contact surface 82 according to the present invention. The first cap 82 has a cap portion 90 which, in this illustrative embodiment, has a hexagonally-shaped receptacle 91 in its bottom to receive the hexagonal top 66 of the implant fixture 60. (Of course, if the fixture top 66 is not hexagonal, the receptacle 91 will have a shape complementary to the top 66.) Above the cap portion 90 is a contact surface 92. In this illustrative embodiment, the contact surface 92 is generally spherical. However, the surface may be any surface allowing rotational contact with the deformable cap 84. The top of the contact surface 92 has an opening 94 which extends longitudinally through the length of the first cap 82 so that a screw may extend through. The opening 94 may have a narrowing 96 to support a countersunk screwhead. The opening 94 may be threaded above the narrowing 96 for securing a threaded screw. An indent 98 is located between the cap 90 and contact surface 92. The first cap 82 maybe made of stainless steel or other sturdy biocompatible material. The contact surface 92 preferably has a slightly coarse, textured surface. The reason for this will become apparent with the following discussion.

FIGS. 12–15 show an illustrative embodiment of a deformable cap according to the present invention. The deformable cap 84 has a number of deformable portions 100 terminating with inwardly directed detents 102. The deformable portions 100 are separated by openings 103. A top 104 has an opening 106 through which a screw may extend. The opening may be chamfered 108 to receive the head of a countersunk screw.

Figure 16:
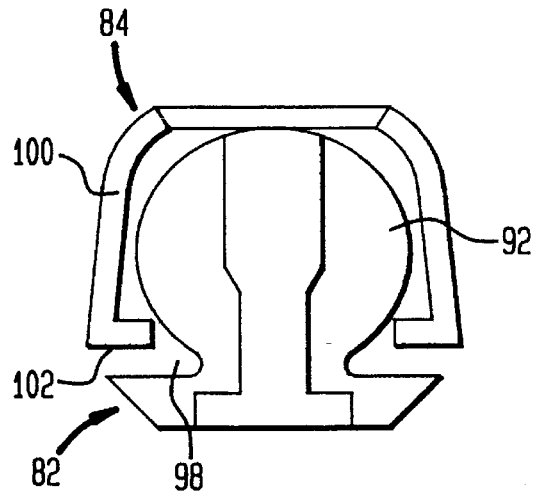
FIG. 16 is a cross-sectional view of a deformable cap in position on a spherical cap according to the present invention.

FIG. 16 shows an illustrative embodiment of the deformable cap in place over a first cap 82 having a spherical contact surface. The deformable cap 84 fits over the first cap 82 so that the inwardly directed detents 102 extend into indent 98. The deformable cap 84 is loosely held on the spherical cap 82 and may be freely rotated thereon. The deformable cap 84 may be made of stainless steel or other biocompatible material that is relatively rigid yet deformable.

Figure 17:
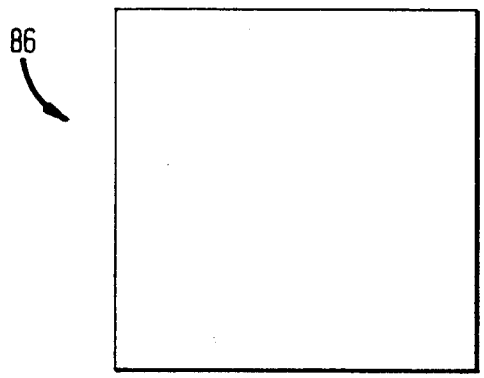
FIG. 17 is a side elevational view of a overcap according to the present invention.
Figure 18:
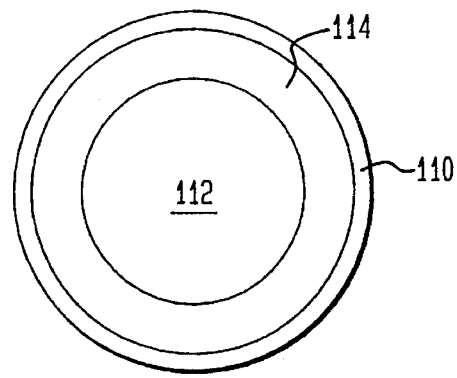
FIG. 18 is a top view of the overcap of FIG. 17.
Figure 19A:
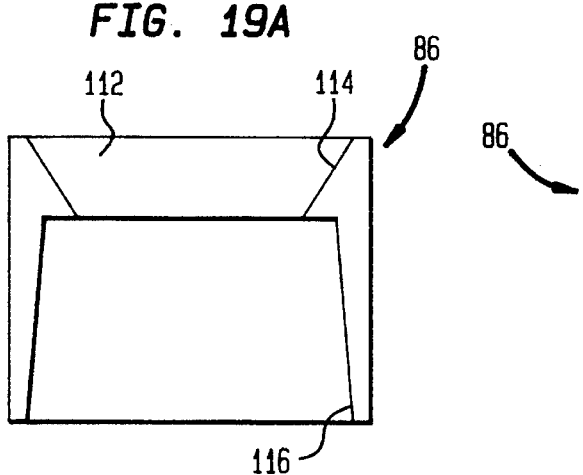
FIGS. 19(a) and 19(b) are cross-sectional views of alternative embodiments of the overcap of FIG. 17.
Figure 19B:
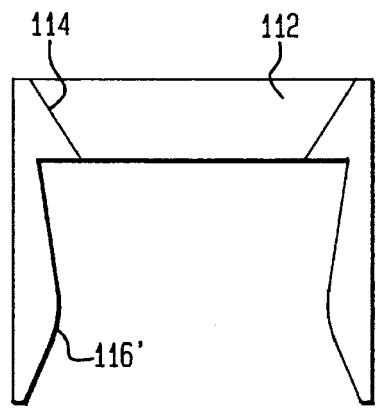

FIGS. 17–19 show illustrative embodiments of an overcap according to the present invention. The overcap 86 has a top 110. The top 110 has an opening 112 with an oversided chamfer 114. The purpose of this oversized chamfer 114 will become apparent after the discussion below. The overcap 86 is hollow and its inner surface is shaped to contact the deformable cap 84 and to compress the deformable members 100 against the contact surface 92. Two illustrative examples of the inner surface are shown. The overcap 86 of FIG. 19(*a*) has an inner surface 116 with a ramped shape which gradually increases from bottom to top. When inserted over the deformable cap 84, the upper portion of the inner surface 116*a* will compress the deformable members 1 00 into contact with the contact surface 92. The overcap of FIG. 19(*b*) has a generally hourglass shape which increases from the bottom towards the middle and then decreases from the middle towards the top. In this embodiment, the middle portion of the inner surface 116*b* compresses the deformable members 100. It is apparent to one skilled in the art that a variety of inner surface configurations provide an overcap which will contact and compress the deformable arms 100 of the deformable cap 84. The overcap 86 preferably has an outer surface configuration approximately the same as a dental prosthesis to be attached to the implant fixture. The overcap shown in FIGS. 18–19(*b*) may be made of suitable biocompatible material such as titanium, plastic, or stainless steel.

Figure 20:
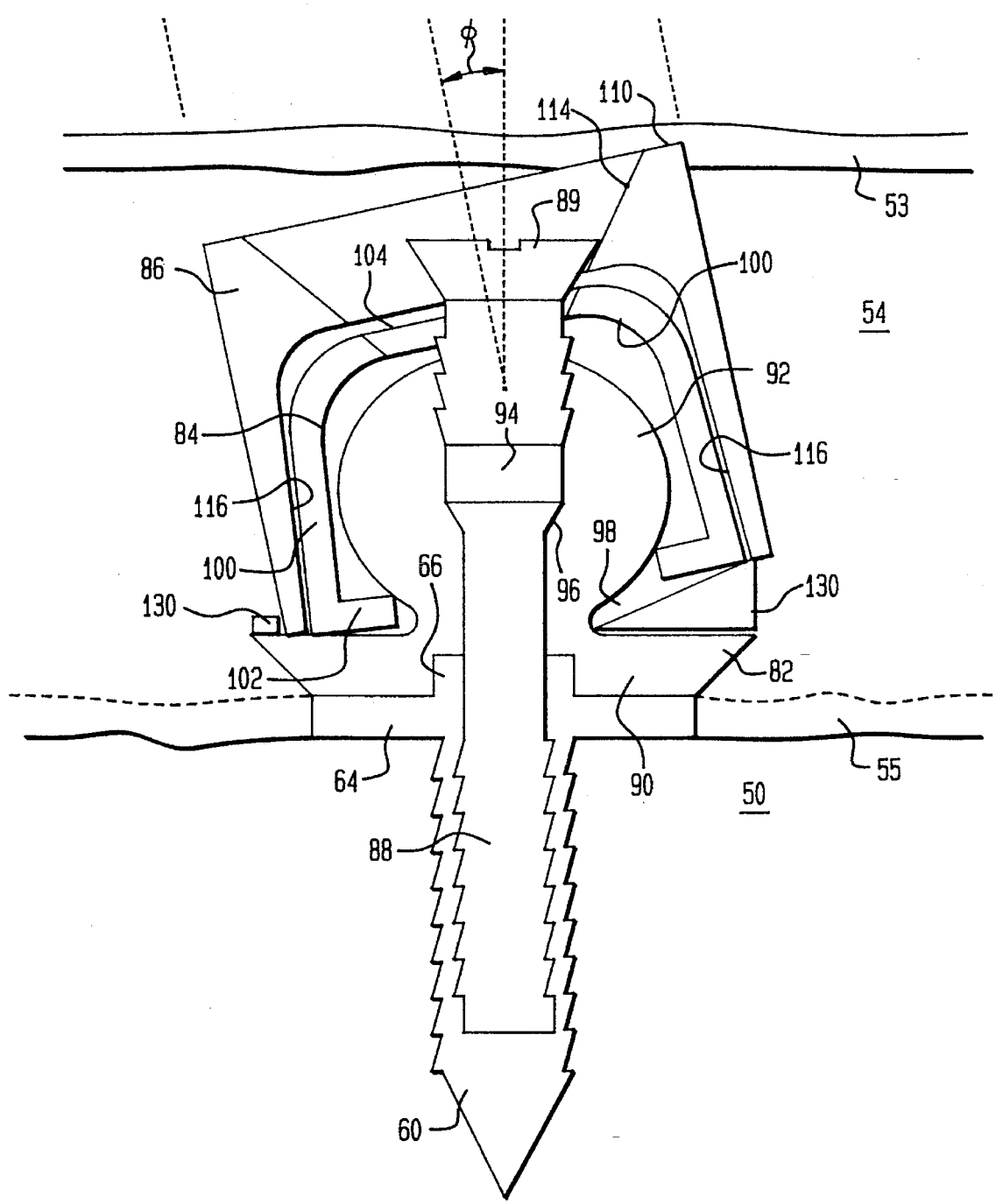
FIG. 20 is a cross-sectional view of a dental implant fixture having a healing abutment according to the present invention in place in a patient.

FIG. 20 shows an implant fixture in place in a mandible and having a healing abutment according to an illustrative embodiment of the present invention attached. An implant fixture 60 is positioned in a mandible 50 and having a circular portion 64 and a hexagonal head 66. A first cap 82 fits over the hexagonal head 66 to securely seat the first cap 82 on the implant fixture 60 and prevent the first cap 82 from rotating. A screw 88, for example, a gold dental screw, is inserted through opening 94 in the cap with spherical portion 82 so the countersunk head rests against ramped portion 96. The threads of screw 88 engage with the threaded portion of the opening in the implant fixture.

A deformable cap 84 is positioned over the contact surface 92. Deformable portions 100 extend down over the contact surface 92 so that inwardly directed detents 102 extend into indent 98 in the contact surface.

The deformable cap 84 sits loosely on the contact surface 92 and is free to be positioned at a desired angle. In this illustration, it is desirable to position a dental prosthetic at an angle φ from the longitudinal axis of the implant fixture 60. The deformable cap 86 is positioned accordingly, as illustrated. An overpiece 86 is inserted over the properly positioned deformable cap 84. The overcap's inner surface 116 contacts the deformable arms 100 which compress the arms 100 into contact the contact surface 92. Because the contact surface 92 preferably has a slightly rough texture, a friction fit holds the deformable cap 84 in the desired location. A second screw 89 is screwed into a threaded opening 94 in the first cap 82 to retain the deformable cap 84 and overcap 86 in position. The oversized chamfer 116 in the top 110 of the overcap 86 allows the second screw 89 to be screwed down into the opening 94 in the contact surface 92 regardless of the angle of the healing abutment with respect to implant fixture 60.

Figure 21:
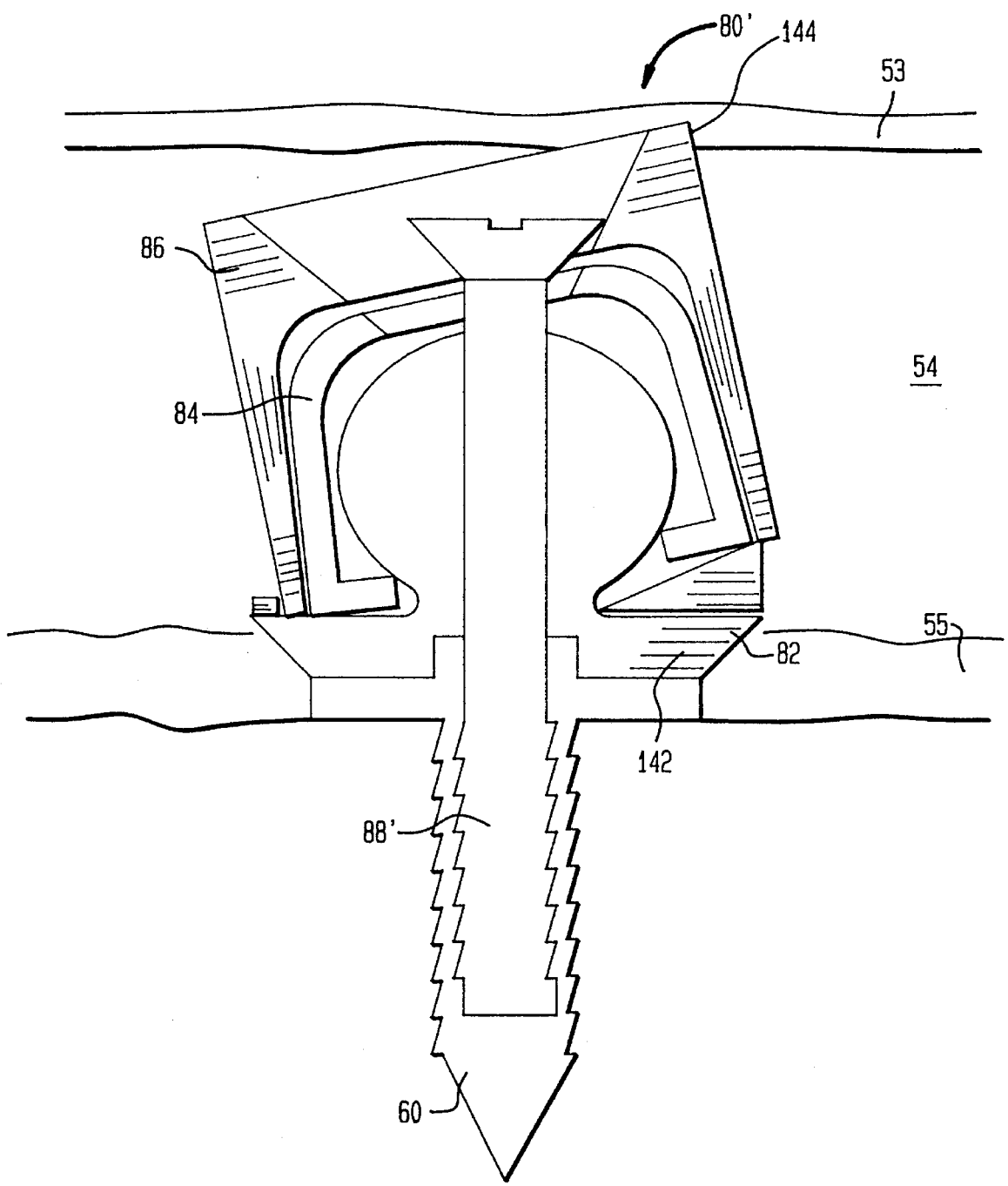
FIG. 21 is a cross-sectional view of second embodiment of a dental implant healing abutment according to the present invention.

In FIG. 21, the healing abutment 80 is configured so that a single screw 88' extends from the outer cap 86 to the implant fixture 60. The opening in the first cap 82 need not be threaded. The oversized chamfer 116 of the overcap 86 allows the screw to be inserted regardless of the angle.

As shown in FIG. 20, the healing abutment 80 is at an angle φ with respect to the fixture 60. The soft tissue will heal around the healing abutment 80. Because the healing abutment preferably has an outer configuration approximately the same as a dental prosthesis to be placed on the implant fixture, the soft tissue heals in all areas except for where the permanent abutment and dental prosthetic will be placed. Thus, there is no unsightly gap in the soft tissues for food particles to collect.

As shown in FIG. 20, the healing abutment may also have a collar 130 which may be inserted between the circular portion 90 of the first cap 82 with the contact surface 92 and the bottom portions of the inwardly directed detents 102 and the bottom of the overcap 86. This collar will fill in any exposed portion of the indent 98 in which soft tissue could grow.

Figure 22:
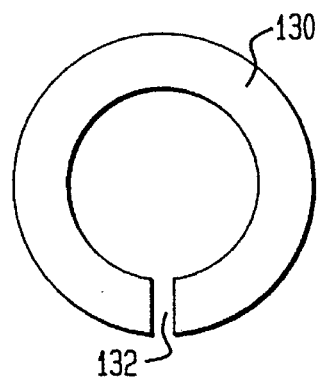
FIG. 22 is a top view of a healing abutment collar according to the present invention.
Figure 23A:
FIGS. 23(a), (b) and (c) are side views of alternative embodiments of the collar of FIG. 22.
Figure 23B:
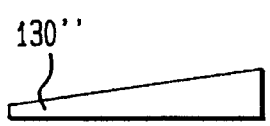
Figure 23C:

As shown in FIGS. 22 and 23, an illustrative embodiment of the collar 130 is an annular ring having a gap 132 which allows the collar to be positioned around the healing abutment. As seen in FIG. 23, the ring may come in a variety of shapes, depending on the angle of the healing abutment 80 with respect to the implant fixture 60. For example, if the longitudinal axes of the implant fixture 60 and healing abutment 80 are aligned (i.e., the angle φ=0°), then the collar will have a uniform height, as shown by the collar 130' of FIG. 23(*a* ). As the angle φ increases, the height of one side of the collar will increase and the other decrease proportionally. For example, FIG. 23(*b*) shows a collar 130' for a moderate angle and FIG. 24(*c*) shows a collar 130" for a large angle. The collar is preferably made of a flexible, biocompatible material such as silicon, plastic, Teflon or the like.

Figure 24:
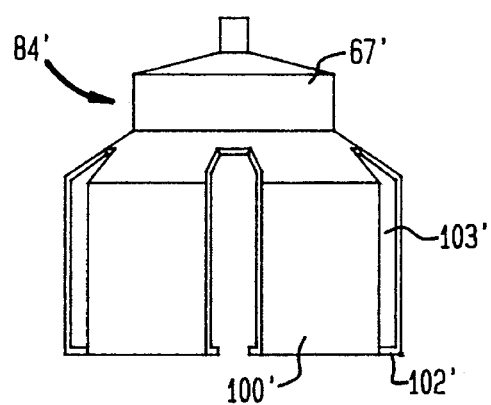
FIG. 24 is an alternative embodiment of a deformable cap according to the present invention.

FIG. 24 illustrates an alternative embodiment of the deformable cap according to the present invention. A deformable cap 84' has an abutment head 67' shaped to receive an artificial tooth.

Figure 25:
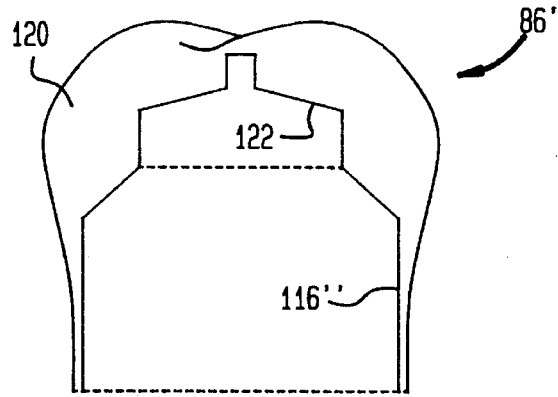
FIG. 25 is an overcap configured as a temporary tooth according to an embodiment of the present invention.

FIG. 25 shows an alternative embodiment of an overcap according to the present invention. The alternative overcap 86' is a temporary prosthetic tooth which fits over the deformable member shown in FIG. 24. The exterior 20 is shaped, colored, and textured to resemble a tooth. The hollow inner portion has a ramped surface 116" and a receptacle 122 for receiving the tip of the abutment 67' shown in FIG. 24. The artificial tooth may be made of any suitable biocompatible material used for dental prosthetic such as ceramic or plastic.

Research has uncovered that varying the external texture of healing abutments depending on the soft tissue layer results in guided tissue regeneration. This research is reported in, for example, *Generation of New Bone Around Titanium Implants Using A Membrane Technique*, C. Dahlin, L. Sennerby, U. Lekholm, et al., Journal of Oral Maxillofacial Implants 4:18 (1989); and *Guided Bone Regeneration Next to Osseointegrated Implants in Humans*, H. C. Wachtel, A. Langford, J. L. Bernimoulin, et al., Journal of Maxillofacial Implants 6:127 (1991). Therefore, it would be advantageous for the healing abutment 86 having an external surface with various textured surfaces in order to have the benefits of guided tissue regeneration. The healing abutment in FIG. 21 is shown with such a textured surface. As illustrated in the exemplary embodiment in FIG. 21, an inferior region 142 of the healing abutment and implant, which contacts the periosteum layer 55, has a generally horizontally oriented texture. A medial portion 144 of the healing abutment, which contact, the connective tissue 54, has a generally vertically oriented texture. A superior portion 144, which contacts the epithelium 53, has a generally horizontally oriented texture. The collar 130 and cap portion 90 of the first cap 82 may also have textured surfaces as shown in FIG. 21.

While the invention has been described by the reference to specific embodiments, this was for purposes of illustration only and should not be construed to limit the spirit or the scope of the invention.

I claim:

1. A dental implant healing abutment, comprising:

(a) a contact surface connectible to an implant fixture and having a generally spherical portion and a longitudinal opening extending entirely through the contact surface;

(b) a first cap first and to connected to the contact surface in a manner to selectively rotate the cap to a desired angle with respect to the implant fixture; the first cap having a first top, the first top having a first opening; the first opening aligned being with the longitudinal opening; and (c) an overcap having an external configuration generally similar to a dental prosthesis and an inner surface designed to contact and compress the deformable cap into secure contact with the contact surface said overcap overlying and in contact with the first cap, and having a second top having a second opening; the second opening aligned with the longitudinal opening and the first opening regardless of the angle between the implant fixture and the deformable cap; whereby a screw may extend through the longitudinal opening, the first opening, the second opening, and enter the implant fixture.

2. The healing abutment of claim 1, wherein the contact surface has a coarse texture.

3. The healing abutment of claim 1, wherein the contact surface includes:

(a) a second cap portion configured to securely connect to the implant fixture; and (b) an indent defined between the cap portion and the generally spherical portion.

4. The healing abutment of claim 3, wherein the first cap includes inwardly directed detents configured to extend into the indent when the first cap is selectively, rotationally connected to the contact surface.

5. The healing abutment of claim 3, further including a collar for insertion in the indent around the contact surface and below the first cap and overcap.

6. The healing abutment of claim 3, further including a collar configured to fill in exposed portions of the indent.

7. The healing abutment of claim 1, wherein the first cap includes a plurality of deformable members.

8. The healing abutment of claim 7, wherein the deformable members include inwardly directed detents.

9. The healing abutment of claim 1, wherein the first cap includes a head for receiving a dental prosthesis.

10. The healing abutment of claim 9, wherein the overcap is configured as a dental prosthesis and has a receptacle for receiving the deformable cap head.

11. The healing abutment of claim 1, wherein the overcap is hollow and has a ramped inner surface.

12. The healing abutment of claim 1, wherein the overcap is hollow and has a generally hourglass-shaped inner surface.

13. The healing abutment of claim 1, wherein an external surface of the healing abutment is textured to promote guided tissue regeneration.

* * * * *